(12) United States Patent
Bergmann et al.

(10) Patent No.: US 6,274,128 B1
(45) Date of Patent: Aug. 14, 2001

(54) SELF-WARMING HAIR CONDITIONING COMPOSITIONS

(75) Inventors: Wolfgang Robert Bergmann, Long Grove; Ben Janchitraponvej, Niles; Trefor Evans, Lombard, all of IL (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/220,475

(22) Filed: Dec. 23, 1998

(51) Int. Cl.$^7$ ............... A61K 7/06; A61K 7/00; A61K 31/74
(52) U.S. Cl. ............ 424/70.1; 424/78.02; 424/400; 424/401; 574/880; 574/881
(58) Field of Search ............... 424/70.1, 70.2, 424/70.31, 70.11, 70.16, 70.17, 78.03; 514/880, 881

(56) References Cited

U.S. PATENT DOCUMENTS

| | | | |
|---|---|---|---|
| 3,250,680 | * 5/1966 | Menkart | 167/85 |
| 3,702,302 | 11/1972 | Wilson | 252/70 |
| 4,902,499 | 2/1990 | Bolish, Jr. et al. | 424/70 |
| 5,328,685 | 7/1994 | Janchitraponvej et al. | 424/71 |
| 5,385,729 | * 1/1995 | Prencipe et al. | 424/70.11 |
| 5,580,550 | 12/1996 | Gough et al. | 424/70.11 |
| 5,656,280 | 8/1997 | Herb et al. | 424/401 |

FOREIGN PATENT DOCUMENTS 0586929  3/1994  (EP).
0897719  2/1999  (EP).

OTHER PUBLICATIONS

Biore' Self–heating mask (Product label–2 pages—copyright 1998).
International Search Report Application No. PCT/EP 99/10168 mailed May 11, 2000.
H.F. Mark: "Kirk–Othmer Encyclopedia of Chemical Technology", vol. 15—1978—XP002133448; pp. 638–648 and p. 660; table 6.
H.F. Mark: "Kirk–Othmer Encyclopedia of Chemical Technology"—P002133449; p. 115 and pp. 122–124.
H.F. Mark: "Kirk–Othmer Encyclopedia of Chemical Technology", vol. 1—1978; pp. 563–564—P002133655.

* cited by examiner

Primary Examiner—Shelley A. Dodson
(74) Attorney, Agent, or Firm—Matthew Boxer

(57) ABSTRACT

An essentially anhydrous hair conditioning composition comprising:
 (a) one or more microporous materials each of which has an average pore size larger than the critical diameter of a water molecule;
 (b) carrier molecules or molecular aggregates that have critical diameters larger than the largest average pore size of the microporous materials; and
 (c) conditioner molecules or molecular aggregates that have critical diameters larger than the largest average pore size of the microporous materials.

The invention also relates to a method for conditioning hair with warming which comprises administering to the hair, with water, the hair conditioner compositions of the invention.

28 Claims, No Drawings

SELF-WARMING HAIR CONDITIONING COMPOSITIONS

FIELD OF THE INVENTION

This invention concerns processes and compositions for the treatment of human hair. More particularly the invention concerns a hair conditioner composition and a conditioning shampoo composition that provide a noticeable increase in temperature during use and that provide good conditioning properties to the hair.

BACKGROUND OF THE INVENTION AND PRIOR ART

When treating hair with conditioner, it would be desirable for the conditioner being used to increase in temperature during actual use. More specifically it would be desirable for the conditioner to increase in temperature after being added to hair that is already wet (for example, after shampooing). Alternatively such a conditioner could be added to dry hair and then after water is added, there would be an increase in temperature in said conditioner. Finally, such a conditioner could be put on hair simultaneously with water and the conditioner would increase in temperature. Such increases in temperature are referred in this specification as self warming. Such self-warming would provide the consumer with a feeling of comfort and relaxation, as well as supplying the consumer with a "signal" that the conditioner composition is working.

A self-warming composition which is presently on the market is Lux Super Rich Self Warming Conditioner. It is an anhydrous glycol containing composition which generates heat through the dissolution of the glycol in water. By contrast the compositions of the present invention generate heat when water adsorbs into the pores of the microporous materials. Anhydrous glycol containing products increase in temperature on application of water, 7 to 8 degrees C. under normal conditions of use on the hair. The compositions of the present invention will often increase in temperature significantly more upon application of water during use in the hair.

It is an object of the present invention to provide an improved hair conditioner which provides increased self-warming hair conditioner composition during use (i.e., when applied to hair with water) while not decreasing the conditioning provided, and in some cases increasing the conditioning that is provided.

BRIEF SUMMARY OF THE INVENTION

The invention relates to hair conditioner compositions which are essentially anhydrous that comprise:
  (a) one or more microporous materials each of which has an average pore size larger than the critical diameter of a water molecule;
  (b) carrier molecules or molecular aggregates that have critical diameters larger than the largest average pore size of the microporous materials; and
  (c) conditioner molecules or molecular aggregates that have critical diameters larger than the largest average pore size of the microporous materials.

The invention also relates to a process for treating hair which comprises administering to said hair, the hair conditioner composition described above.

The invention also relates to a conditioning shampoo composition that provides a noticeable increase in temperature during use.

The invention also relates to a process for treating hair which comprises administering to said hair, the conditioning shampoo composition described above.

The hair conditioner compositions of the invention and the conditioning shampoo compositions provide increased self-warming during use (i.e., when applied to hair with water) while not decreasing the hair conditioning provided and in some cases increasing the hair conditioning provided. This is an unexpected result, since the hair conditioner compositions of the invention comprise microporous materials such as molecular sieves which are a solid particulate material which would be expected to decrease the conditioning properties of the compositions of the invention as compared to compositons without microporous materials or molecular sieves. In fact the compositions of the invention have the same or increased conditioning properties as noted above.

DETAILED DESCRIPTION OF THE INVENTION

Hair conditioner compositions of the invention include rinse-off and leave-in conditioners.

As used herein "essentially anhydrous" means less than about 2 weight % preferably less than about 1 weight % of water.

Unless otherwise indicated, as used herein % means weight %. All of the starting materials described herein are either known or can be prepared according to known methods. The essentially anhydrous hair conditioner compositions of the invention comprise:
  (a) one or more microporous materials each of which has an average pore size larger than the critical diameter of a water molecule;
  (b) carrier molecules or molecular aggregates that have critical diameters larger than the largest average pore size of the microporous materials; and
  (c) conditioner molecules or molecular aggregates that have critical diameters larger than the largest average pore size of the microporous materials.

It is noted that each of the one or more microporous materials referred to above has an average pore size larger than the critical diameter of a water molecule. The size of a water molecule is about 3.2 Angstroms. It is also noted that microporous materials with an average pore size of 3 Angstrom are used in compositions described below. Even though some of such microporous materials have too small a pore size to adsorb water, enough of such microporous materials have a large enough pore size to be useful in the compositions of the invention.

The microporous materials may be selected from the group consisting of inorganic salts such as crystalline metal silicates such as sodium potassium aluminum silicate, aluminum silicate, calcium aluminum silicate, activated alumina (aluminum oxide), clays which are silicates, known as diatomaceous silicas, bentonites and clays these are aluminum oxides and silicon oxides, and crystalline metal aluminosilicates. Among the crystalline metal aluminosilicates which may be employed are aluminosilicates which range in average pore size from about 3 Angstroms to about 10 Angstroms.

In general, the average pore size for the sieves that are used in the compositions of the invention can range from about 3 Angstroms to about 13 Angstroms or larger. More preferably, the average pore size of the sieves can range from about 3 Angstroms to about 10 Angstroms.

The tradenames of these aluminum silicates include Aldrich 3A Sieves, Aldrich 10X Sieves, and Sylosiv A3 Sieves, and Sylosiv A4 Sieves.

PQ Corporation is another molecular sieve supplier and the material that they supply, is an aluminosilicate is called Advera 401 N.

Organic resins such as activated charcoal may also be employed where the average pore size of the organic resins meets the parameters described above.

The microporous materials are normally present in a concentration of from 5% to 60%, preferably from 10 to 40% by weight based on the total weight of the hair treatment composition, or more preferably 15 to 30% by weight based on the total weight of the hair treatment composition.

Carrier materials must have a critical diameter larger than the largest average pore size of the microporous materials selected. With respect to the resulting anhydrous hair care composition, as long as most of the pores in the microporous material are unoccupied there will be a heating effect on the addition of water.

The selected carrier materials have to be water soluble or water dispersible otherwise they could not be used on hair in combination with water.

Suitable carrier materials include hydrophilic glycols, polyethylene glycols, and polar solvents like alcohols. Any carrier used must either be water soluble or water dispersible.

The following list of hydrophilic glycols or polyhydric alcohols which may be used in compositions of the invention is meant to be illustrative and not limiting. These hydrophilic glycols are as follows: propylene glycol, ethylene glycol, glycerin, sorbitol, butanediol, butylene glycol, and mixtures thereof.

The following list of polyethylene glycols which may be used in compositions of the invention is meant to be illustrative and not limiting. These polyethylene glycols are as follows: PEGs -4, -6, -8, -9, -10, -12, -14, -16, -18, -20, -200, -400 and -600. Also included are beheneth -5 and -10, peg-7 betanaphthol and PEG-15 butanediol. Also included are buteth-3 carboxylic acid, butoxynol-5 and -19, PEG-8 C12–18 ester, C12–13 pareth-7 carboxylic acid, C11–15 pareth-7 carboxylic acid, C12–15 pareth-7 carboxylic acid, C14–15 pareth-8 carboxylic acid, PEG-8 caprate, PEG-8 caprylate, PEG-8 caprate/caprylate, PEG -6, and -8 caprylic/capric gylcerides, capryleth -6 and -9 carboxylic acids, ate, PEG-8 caprylate. Also included are ceteareth -2, -3, -4, -5, -5, -6, -7, -8, -10, -11, -12, -13, -15, -6, -17, -18, and -20; choleth -10 and -20; PEG-3 cocamide, PEG-5 cocamide, PEG-6 cocamide, PEG-7 cocamide, PEG-11 cocamide, PEG-20 cocamide; PEG-2 cocamine, PEG-3 cocamine, PEG-5 cocamine, PEG-10 cocamine, PEG-15 cocamine, and PEG-20 cocamine; PEG-5 cocoate, PEG-8 cocoate, PEG-15 cocoate; coceth-3, 5, and -8; PEG-2 dilaurate, PEG-4 dilaurate, PEG-6 dilaurate, PEG-8 dilaurate, PEG-12 dilaurate, PEG-20 dilaurate, PEG-4 dioleate, PEG-6 dioleate, PEG-8 dioleate, PEG-10 dioleate, PEG-12 dioleate, and isosteareth-2, isosteareth-3, isosteareth-10, isosteareth-12, and isosteareth-20; isoceteth-10, and -20; isodeceth -4, -5, and -6; isostereath -2, -3, 10, -12, and -20; PEG-3 lauramine oxide; PEG-2 laurate, PEG-4 laurate, PEG-6 laurate, PEG-8 laurate, PEG-9 laurate, PEG-10 laurate, PEG-12 laurate, PEG-14 laurate, and PEG-20 laurate; laureth -1, -2, -3, -4, -5, -6, -7, -8, -9, -10, -11, -12, -13, -14, -15, -16, and -20; oleth 2, -3, -4, -5, -6, -7, -8, -9, -10, 12, -15, -16, and -20; stereath -2, -3, -4, -5, -6, -7, -10, -11, -13, -14, -15, -16, and -20; and trideceth -3, -5, -6, -9, -10, -11, -12, and -15.

The following list of polar solvents like alcohols which may be used in compositions of the invention is meant to be illustrative and not limiting. These polar solvents like alcohols are as follows: methanol, ethanol, propanol, butanol, pentanol, hexanol, heptanol and isopropanol and mixtures thereof.

Carrier materials may be included in compositions of the invention in a weight % range of about 40% to about 90%, more preferably about 60 to about 80%.

Conditioner materials are selected from the group consisting of quaternary ammonium compounds, amidoamines, silicones, cationic polymers, hydrocarbons, fatty alcohols, either alone or in combination. Any conditioner material which is used in a composition of the invention must have a critical diameter that is larger than the largest pore average size of the microporous materials.

The following list of silicones which may be used in compositions of the invention is meant to be illustrative and not limiting. These silicones are as follows: a polyalkyl siloxane, a polyaryl siloxane or a polyalkylaryl siloxane.

Mixtures of volatile silicones as cyclotetrasiloxane, cyclopentasiloxane, or cyclohexasiloxane are useful. Mixtures of the nonvolatile silicone compounds are also useful. The so-called "rigid silicones", as described in U.S. Pat. No. 4,902,499, herein incorporated by reference, having a viscosity above 600,000 cs at 20C and a weight average molecular weight of at least about 500,000, also are useful in compositions of the present invention. A phenyltrimethicone also is useful as a nonvolatile silicone compound. Also useful is a mixture of a low molecular weight silicone fluid and a higher molecular weight silicone gum. Silicones which are useful in compositions of the invention are described in U.S. Pat. No. 5,656,280 which is hereby incorporated by reference.

Nonvolatile silicones include siloxane or siloxane mixtures having a viscosity of greater than 10 centistokes. Nonlimiting examples include dimethicone, dimethiconol, amodimethicones, phenyl trimethicone and silicone copolyols.

The following list of cationic polymers which may be used in compositions of the invention is meant to be illustrative and not limiting. These cationic polymers are as follows: Guar hydroxypropyltrimonium chloride, poly (dimethyldiallylammonium chloride), poly(dimethyl butenyl ammonium chloride)- bis (triethanolammonium chloride), Poly (dipropyldiallylammonium chloride), Poly (methyl-beta propaniodiallylammonium chloride), Poly (diallylpiperidinium chloride), Poly (vinyl pyridinium chloride), quaternised poly (vinyl alcohol), quaternised poly (dimethylaminoethylmethacrylate) and mixtures thereof. These cationic polymers are described in U.S. Pat. No. 5,580,550 which is hereby incorporated by reference.

The following list of hydrocarbons which may be used in compositions of the invention is meant to be illustrative and not limiting. These hydrocarbons are as follows: nonane, octane, heptane, tert-pentane, dodecane, decahexane, decane, heptadecane, trimethylheptane, trimethylhexane, 4-methylheptane, 4-methyldecane, isobutane, isopentane, isooctane, hexane, isododecane, polydecene, mineral oil, paraffin wax and isohexadecane. Other exemplary volatile hydrocarbons are depicted in the general structural formula I wherein n ranges from 2 to 5.

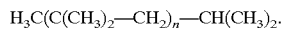

Another exemplary hydrocarbon is ISO-PAR M (a C13–C14 isoparaffin available from Exxon Chemical Co. Baytown Tex.). These compounds are described in U.S. Pat. No. 5,656,280 which is hereby incorporated by reference. Also included among volatile hydrocarbons which can be used in compositions of the invention are mineral oil, paraffins, fatty acids, caprylic/capric triglyceride, caprylic/capric diglyceryl succinate, propylene glycol dicaprylate/dicaprate, mineral jelly, acetylated lanolin, M-quat 40, oil soluble lipo-protein, collagen/lanolin oil blend, mineral oil and lanolin alcohol, cetyl acetate, lanolin oil, isopropyl palmitate and lanolin oil, silk powder, decyl neopentanate, jojoba oil, and propoxylated polyol.

The following list of quaternary ammonium compounds which may be used in compositions of the invention is meant to be illustrative and not limiting. These compounds have the general structural formula: $N[R_1R_2R_3R_4]+X-$ where $R_1$ is an alkyl group including from about 8 to about 18 carbon atoms, $R_2$ is selected from the group consisting of an alkyl group including from about 8 to about 18 carbon atoms, a hydrogen atom, a methyl group, an ethyl group, a hydroxymethyl group and a hydroxyethyl group, $R_4$ is selected from the group consisting of a hydrogen atom, a methyl group, an ethyl group, a hydroxymethyl group, and a hydroxyethyl group; and X is an anion. The quaternary nitrogen of the quaternary ammonium compound can also be a component of a heterocyclic moiety such as morpholine or pyridine. The anion can be an anion such as chloride, methosulfate, ethosulfate, nitrate, bromide, tosylate, acetate or phosphate.

The quaternary ammonium compounds have one or two long chain alkyl groups having from about 8 to about 18 carbon atoms. The long chain alkyl groups can also include in addition to, or in replacement of carbon and hydrogen atoms, ether linkages or similar water solubilizing linkages the remaining two or three substituents of the quaternary nitrogen can be hydrogen or benzyl; or short chain alkyl or hydoxyalkyl groups such as methyl ethylhydroxymethyl or hydroxyethylgroups, or combinations thereof either diteher of the same or different identity.

Exemplary quaternary ammonium compounds include but are not limited to lauratrimonium chloride, quaternium -16, lauralkonium chloride, dicetyldimonium chloride, cetylpyridinium chloride, soyatrimonium chloride, mytrimonium chloride, cetrimonium chloride, PEG-2 cocomonium chloride, PEG 2 cocoyl quaternium -4, PEG 2 oleyl quarenium 4 polyquaternium -6, -7, -11, -5, -24, and mixtures thereof. These quaternary ammonium compounds are described in U.S Pat. No. 5,656,280 which is hereby incorporated by reference. Other water-soluble ammonium compounds include distearyl dimonium chloride, and behenyl trimmonium chloride.

The following list of amidoamines which may be used in compositions of the invention is meant to be illustrative and not limiting. These amidoamines Include those described in U.S. Pat. No. 5,328,685 which is hereby incorporated by reference.

Amidoamines include but are not limited to diethylaminoethylstearamine, isosteamidopropyldimethylamine, cocamidopropyldimethylamine, ricinoleamido propyldimethylamine, oleamidopropyidimethylamine, behenamidopropyldimethylamine, palmitamidopropyldimethylamine, stearamidoethyldiethylamine, stearamidylpropyidiethylamine, stearamidopropyidimethylamine soyamido—propyldimethylamine and dimethylaminopropyl myristamide.

The following list of fatty alcohols which may be used in compositions of the invention is meant to be illustrative and not limiting. These fatty alcohols include a fatty alcohol or fatty acid, or derivative thereof, or a mixture of any of these having a chain length of from about 8 to about 36 carbon atoms. More preferably from about 12 to about 18 carbon atoms. These materials may be predominantly linear or may be branched. Preferred are stearyl alcohol, cetyl alcohol, behenyl alcohol, lauryl alcohol, myristyl alcohol, and coco alcohol.

Conditioner materials may be included in compositions of the invention in a weight per cent range of about 2% to about 45%, more preferably about 10 to about 30%.

Optional ingredients which can be used in compositions of the invention are now described.

Nonionic surfactants suitable for use in compositions of the invention include condensation products of aliphatic $C_8$–$C_{18}$ primary or secondary linear or branched chain alcohols or phenols with alkylene oxides, usually ethylene oxide, and generally having from 6 to 30 ethylene oxide groups.

Other suitable nonionics include mono- or di-alkyl alkanolamides. Examples include coco mono- or diethanolamide and coco mono-isopropanolamide. Further suitable nonionic surfactants are the alkylpolyglycosides (APG's). Typically, the APG is one which comprises an alkyl group connected (optionally via a bridging group) to a block of one or more glycosyl groups.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms.

Examples include lauryl amine oxide, cocodimethyl sulphopropyl betaine and preferably lauryl betaine, cocamidopropyl betaine and sodium cocamphopropionate.

Further surfactants which may be suitable for use in conditioning shampoos in accordance with the invention include one or more anionic surfactants instead of or in addition to any of those surfactants mentioned above. Those surfactants must be dispersed or mixed in glycols, PEGs, etc.

Suitable anionic surfactants are the alkyl sulphates, alkyl either sulphates, alkaryl sulphonates, alkaroyl isethionates, alkyl succinate, alkyl sulphosuccinates, N-alkoyl sarcosinates, alkyl phosphates, alkyl ether phosphates, alkyl ether carboxylates, and alpho-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

As further optional components for inclusion in the compositions of the invention, the following may be mentioned: pH adjusting agents, viscosity modifiers, cosmetic fillers such as talc, kaolin; peariescers, opacifiers, suspending agents, preservatives, coloring agents, dyes, proteins, herb and plant extracts, polyols and other moisturizing.

Compositions of the invention can be made by using processes which are known in the art or by using processes which are analogous to those known in the art. Compositions of the invention can be made by using starting materials which are known in the art or by using starting materials which are obtainable from materials that are known in the art.

Compositions of the invention are used in a manner known for leave-in and wash-out conditioners. Namely, the hair is wet and then conditioner or conditioning shampoo is applied to the hair.

If the conditioner is a leave-in conditioner, it can be applied to wet or dry hair. If applied to dry hair, then water is added after such application. If the conditioner is a wash-out conditioner, the hair is the rinsed after application.

The self-warming that occurs with the use of the hair conditioner compositions arises when water molecules adsorb into the pores of the microporous materials. This step releases heat which is felt as self-warming. Up to a 17° C. increase or more, typically increases of 15° C. or more are achieved with compositions of the invention. 12° C. increase or more, or increases of 10° C. or more can also be achieved with compositions of the invention. The temperature increase, being referred to above, which is caused by compositions of the invention is the change which occurs in degrees C when 70 parts of composition is mixed with 30 parts water at room temperature.

Compositions of the invention are made by processes known in the art, or analogous to those known in the art using starting materials which are known in the art.

Ingredients which are used in compositions of the invention may fall within the following ranges of weight ratios:

| INGREDIENT | WEIGHT % |
|---|---|
| microporous materials | 5–60 |
| carrier ingredients | 20–80 |
| conditioner ingredients | 1–30 |

Examples of the invention shown below are made by processes known in the art, or analogous to those known in the art. Examples of the invention are as follows:

EXAMPLE 1

Comparative Example

Conditioner—without Molecular Sieves or Other Microporous Materials

| INGREDIENT | WEIGHT % |
|---|---|
| PEG 200 | 71.15 |
| CETEARYL ALCOHOL | 2.5 |
| BEHENTRIMONIUM CHLORIDE | 2.0 |
| STEARETH-2 | 1.0 |
| STEARETH-21 | 1.0 |
| GLYCERIN | 18.6 |
| PANTHENOL | 0.1 |
| DIMETHICONE | 3.0 |
| FRAGRANCE | 0.65 |

EXAMPLE 2

Conditioner with Molecular Sieves or Microporous Material

| INGREDIENT | WEIGHT % |
|---|---|
| PEG 200 | 50.45 |
| CETEARYL ALCOHOL | 2.5 |
| BEHENTRIMONIUM CHLORIDE | 2.0 |
| STEARETH-2 | 1.0 |
| STEARETH-21 | 1.0 |
| PANTHENOL | 0.1 |
| GLYCERIN | 18.6 |
| CITRIC ACID | 0.7 |
| DIMETHICONE | 3.0 |
| SODIUM POTASSIUM ALUMINO-SILCATE 3 Angstroms | 20.0 |
| FRAGRANCE | 0.65 |

EXAMPLE 3

Conditioner with Molecular Sieves or Microporous Materials

| INGREDIENT | WEIGHT % |
|---|---|
| PEG 200 | 55.45 |
| CETEARYL ALCOHOL | 2.5 |
| BEHENTRIMONIUM CHLORIDE | 2.0 |
| STEARETH-2 | 1.0 |
| STEARETH-21 | 1.0 |
| GLYCERIN 99.7% | 18.6 |
| PANTHENOL | 0.1 |
| CITRIC ACID | 0.7 |
| DIMETHICONE | 3.0 |
| SODIUM POTASSIUM ALUMINO-SILICATE 3 Angstroms | 15.0 |
| FRAGRANCE | 0.65 |

EXAMPLE 4

Conditioner with Microporous Materials or Sieves

| INGREDIENT | WEIGHT % |
|---|---|
| PEG 200 | 51.15 |
| CETEARYL ALCOHOL | 2.5 |
| BEHENTRIMONIUM CHLORIDE | 2.0 |
| STEARETH-2 | 1.0 |
| STEARETH-21 | 1.0 |
| GLYCERIN 99.7% | 18.6 |
| PANTHENOL | 0.1 |
| DIMETHICONE | 3.0 |
| SODIUM POTASSIUM ALUMINO-SILCATE 3 Angstroms | 20.0 |
| FRAGRANCE | 0.65 |

EXAMPLE 5

Self-warming Shampoo can be Prepared with Ingredients in the Following Ranges:

| INGREDIENT | WEIGHT % |
|---|---|
| PEG-200 | qs to 100 |
| DIMETHICONE | .5 to 1 |
| SILICA | .1 to 5 |
| GUAR HYDROXYPROPYLTRIMONIUM | .05 to 1 |

-continued

| INGREDIENT | WEIGHT % |
|---|---|
| CHLORIDE | |
| LAURYL HYDROXYETHYL IMIDAZOLINE 100% | 5 to 50 |
| SODIUM POTASSIUM ALUMINOSILICATE A3 | 20 |
| ADDITIVES | .01 to 5 |

TABLE I

| COMPOSITION | WET COMBING TOTAL ENERGY mi | WET COMBING MAX LOAD G FORCE |
|---|---|---|
| EXAMPLE 1 | 12.97 | 14.48 |
| EXAMPLE 2 | 11.93 | 12.97 |

The above table Idemonstrates that compositions of the invention which comprise molecular sieves (example 2) have the same or even better wet combing properties than compositions without sieves (example 1) and that therefore, the compositions of the invention have the same or even better conditioning properties than compositions without molecular sieves.

TABLE II

Summary of Self Warming Compositions-Effect of Molecular Sieve Addition

| COMPOSITION | WATER DILUTION TEMP. IN DEGREES C.[1] | PORE SIZE IN ANGSTROMS | WT % MOL. SIEVES |
|---|---|---|---|
| 100% PEG 200 | +8 | NA[2] | 0% |
| 100% GLYCERIN | 0 | NA | 0% |
| 90% PEG 200 + 10% ALDRICH 3A[4] | +11 | 3 | 10% |
| 90% GLYCERIN + 10% ALDRICH 3A | +6 | 3 | 10% |
| 90% PEG 2009 + 10% ALDRICH 13X[4] | +10 | 9–10 | 10% |
| 90% GLYCERIN + 10% ALDRICH 13X | +9 | 9–10 | 10% |
| 90% PEG 200 + 10% ZEOLEX 35-P[5] | +10 | NA | 10% |
| 90% GLYCERIN + 10% ZEOLEX 35-P | 0 | NA | 10% |
| 90% PEG 200 + 10% SYLOSIV 3A[3] | +19 | 3 | 10% |
| 90% GLYCERIN + 10% SYLOSIV 3A | +11 | 3 | 10% |
| CONDITIONER EXAMPLE 1 (comparative example without molecular sieves) | +7 | NA | 0% |
| CONDITIONER EXAMPLE 2 | +18 | 3 | 20% |
| CONDITIONER EXAMPLE 3 | +11 | 3 | 15% |
| CONDITIONER EXAMPLE 4 | +18 | 3 | 20% |

TABLE NOTES
[1]Water dilution temp increase is the change in temperature in degrees C. when 70 parts of composition is mixed with 30 parts of water.
[2]NA is not applicable.
[3]Sylosiv 3A is a tradename of the molecular sieves supplied by WR Grace.
[4]Aldrich 13X and Aldrich 3A are tradenames of molecular sieves supplied by Aldrich Chemical.
[5]ZEOLEX 35-P is a tradename of amorphous sodium aluminosilicate supplied by JM Huber.

The above table II demonstrates that compositions of the invention (examples 2,3,4) raise temperature on mixing with water significantly more degrees C. than compositions without molecular sieves and microporous materials (example 1). In addition it demonstrates the need for appropriate selection of microporous materials with carrier.

We claim:

1. A hair conditioner composition which is essentially anhydrous that comprises:
   (a) one or more microporous materials each of which has an average pore size larger than the critical diameter of a water molecule;
   (b) carrier molecules or molecular aggregates that have critical diameters larger than the largest average pore size of the microporous materials; and
   (c) conditioner molecules or molecular aggregates that have critical diameters larger than the largest average pore size of the microporous materials.

2. A composition according to claim 1 wherein the microporous material is an inorganic salt selected from the group consisting of sodium aluminum potassium silicate, aluminum silicate, calcium aluminum silicate, activated alumina (aluminum oxide), diatomaceous silicas, bentonites, aluminum oxides, silicon oxides, and crystalline metal aluminosilicates.

3. A composition according to claim 2 wherein the microporous material is an aluminosilicate which ranges in average pore size from about 3 Angstroms to about 10 Angstroms.

4. A composition according to claim 1 wherein the microporous material is an activated charcoal.

5. A composition according to claim 1 wherein the carrier material is selected from the group consisting of hydrophilic glycols, polyethylene glycols, glycerin, and a polar solvent.

6. A composition according to claim 5 wherein the hydrophilic glycol is selected from the group consisting of propylene glycol, ethylene glycol, hexylene glycol, glycerin, sorbitol, butanediol, butylene glycol, and mixtures thereof.

7. A composition according to claim 5 wherein the polyethylene glycol is selected from the group consisting of PEGs-4, -6, -8, -9, -10, -12, -14, -16, -18, -20, -200, -400 and -600; beheneth -5 and -10; PEG-7 betanaphthol and PEG-15 butanediol; buteth-3 carboxylic acid, butoxynol-5 and -19, PEG-8 C12–18 ester, C12–13 pareth-7 carboxylic acid, C11–15 pareth-7 carboxylic acid, C12–15 pareth-7 carboxylic acid, C14–15 pareth-8 carboxylic acid, PEG-8 caprate, PEG-8 caprylate, PEG-8 caprate/caprylate, PEG-6, and -8 caprylic/capric gylcerides, capryleth-6 and -9 carboxylic acids, PEG-8 caprylateP; ceteareth -2, -3, -4, -5, -5, -6, -7, -8, -10, -11, -12, -13, -15, -6, -17, -18, and -20; choleth-10 and -20; PEG-3 cocamide, PEG-5 cocamide, PEG-6 cocamide, PEG-7 cocamide, PEG-11 cocamide, PEG-20 cocamide; PEG-2 cocamine, PEG-3 cocamine, PEG-5 cocamine, PEG-10 cocamine, PEG-15 cocamine, and PEG-20 cocamine; PEG-5 cocoate, PEG-8 cocoate, PEG-15 cocoate; coceth-3, 5, and -8; PEG-2 dilaurate, PEG-4 dilaurate, PEG-6 dilaurate, PEG-8 dilaurate, PEG-12 dilaurate, PEG-20 dilaurate, PEG-4 dioleate, PEG-6 dioleate, PEG-8 dioleate, PEG-10 dioleate, PEG-12 dioleate, isosteareth-2, isosteareth-3, isosteareth-10, isosteareth-12, isosteareth-20; isoceteth-10, and -20; isodeceth -4, -5, and -6; isostereath-2, -3, 10, -12, and -20; PEG-3 lauramine oxide; PEG-2 laurate, PEG-4 laurate, PEG-6 laurate, PEG-8 laurate, PEG-9 laurate, PEG-10 laurate. PEG-12 laurate, PEG-14 laurate, and PEG-20 laurate; laureth-1, -2, -3, -4, -5, -6, -7, -8, -9, -10, -11, -12, -13, -14, -15, 16, and -20; oleth 2, -3, -4, -5, -6, -7, -8, -9, -10,12, -15, -16, and -20; stereath-2, -3, -4, -5, -6, -7, -10, -11, -13, -14, -15, -16, and -20; and trideceth-3, -5, -6, -9, -10, -11, -12, and -15.

8. A composition according to claim 5 wherein the polar solvent is selected from the group consisting of methanol, ethanol, propanot, butanol, pentanol, hexanol, heptanol, isopropanol and mixtures thereof.

9. A composition according to claim 1 wherein the conditioner materials are selected from the group consisting of quaternary ammonium compounds, amidoamines. hydrophillic silicones, cationic polymers, hydrocarbons, fatty alcohols, and mixtures thereof.

10. A composition according to claim 9 wherein the silicone is selected from the group consisting of a polyalkyl siloxane, a polyaryl siloxane, a polyalkylaryl siloxane and mixtures thereof.

11. A composition according to claim 10 wherein the silicone is selected from the group consisting of a volatile siloxane such as cyclotetrasiloxane, cylopentasiloxane, cyclohexasiloxane, or mixtures thereof.

12. A composition according to claim 10 wherein the silicone is a group of nonvolatile silicones consisting of dimethicone, dimethiconol, amodimethicone, phenyltrimethicone, silicone copolyol, and mixtures thereof.

13. A composition according to claim 9 wherein the cationic polymer is selected from the group consisting of: Guar hydroxypropyltrimonium chloride, poly (dimethyldiallylammonium chloride), poly(dimethyl butenyl ammonium chloride)-bis (triethanolammonium chloride), Poly (dipropyldiallylammonium chloride), Poly (methyl-beta propaniodiallylammonium chloride), Poly (diallylpiperidinium chloride), Poly (vinyl pyridinium chloride), quaternised poly (vinyl alcohol), quaternised poly (dimethylaminoethylmethacrylate) and mixtures thereof.

14. A composition according to claim 9 wherein the hydrocarbon is selected from the group consisting of nonane, octane, heptane, tert-pentane, dodecane, decahexane, decane, heptadecane, trimethylheptane, trimethylhexane, 4-methylheptane, 4-methyidecane, isobutane, isopentane, isooctane, hexane, isododecane, isohexadecane, and mixtures thereof.

15. A composition according to claim 9 wherein the quaternary ammonium compound is selected from the group consisting of lauratrimonium chloride, quaternium-16, lauralkonium chloride, dicetyldimonium chloride, distearyl dimonium chloride, behenyl dimonium chloride, cetylpyridinium chloride, soyatrimonium chloride, myristyltrimonium chloride, cetrimonium chloride, PEG-2 cocomonium chloride, PEG 2 cocoyl quaternium-4, PEG-2 oleyl quaternium-4, polyquaternium-6, -7, -11, -5, -24, and mixtures thereof.

16. A composition according to claim 14 wherein the amidoamine is selected from the group consisting of diethylaminoethylstearamide, isosteamidopropyldimethylamine, cocamidopropyldimethylamine, ricinoleamido propyldimethylamine, oleamidopropyldimethylamine, behenamidopropyldimethylamine, palmitamidopropyldimethylamine, stearamidylethyldiethylamine, soyamido— propyldimethylamine and dimethylaminopropyl myristamide, stearamidylpropyl dimethylamine.

17. A composition according to claim 9 wherein the fatty alcohol is selected from the group consisting of stearyl alcohol, cetyl alcohol, behenyl alcohol, myristle alcohol, coco alcohol, and mixtures thereof.

18. A composition according to claim 1 which comprises:

| INGREDIENT | WEIGHT % |
|---|---|
| PEG 200 | 50.45 |
| CETEARYL ALCOHOL | 2.5 |
| BEHENTRIMONIUM CHLORIDE | 2.0 |
| STEARETH-2 | 1.0 |
| STEARETH-21 | 1.0 |
| PANTHENOL | 0.1 |
| GLYCERIN | 18.6 |
| CITRIC ACID | 0.7 |
| DIMETHICONE | 3.0 |
| SODIUM POTASSIUM ALUMINO-SILICATE 3 Angstroms | 20.0 |
| FRAGRANCE | 0.65. |

19. A method for conditioning hair with self warming which comprises applying to said hair an effective amount of a composition according to claim 1 and then applying to the hair water.

20. A method for conditioning hair with self warming which comprises applying to said hair water, and then applying to the hair an effective amount of a composition according to claim 1.

21. A hair shampoo composition which is essentially anhydrous that comprises:
(a) one or more microporous materials each of which has an average pore size larger than the critical diameter of a water molecule;
(b) carrier molecules or molecular aggregates that have critical diameters larger than the largest average pore size of the microporous materials; and
(c) shampoo molecules or molecular aggregates that have critical diameters larger than the average largest pore size of the microporous materials.

22. A method for shampooing hair with self warming which comprises applying to said hair water, and then applying to the hair an effective amount of a shampoo composition according to claim 21.

23. A method for shampooing hair with self warming which comprises applying to said hair an effective amount of a shampoo composition according to claim 21, and then applying to the hair water.

24. A hair shampoo and conditioner composition which is essentially anhydrous that comprises:
(a) one or more microporous materials each of which has an average pore size larger than the critical diameter of a water molecule;
(b) carrier molecules or molecular aggregates that have critical diameters larger than the average largest pore size of the microporous materials; and
(c) conditioner molecules or molecular aggregates that have critical diameters larger than the largest average pore size of the microporous materials;
(d) shampoo molecules or molecular aggregates that have critical diameters larger than the average largest pore size of the microporous materials.

25. A method for shampooing and conditioning hair with self warming which comprises applying to said hair water, and then applying to the hair an effective amount of a shampoo and conditioner composition according to claim 24.

26. A method for shampooing and conditioning hair with self warming which comprises applying to said hair an effective amount of a shampoo and conditioner composition according to claim 24, and then applying to the hair water.

27. A composition in accordance with claim 1, wherein the average pore size is from about 3 Angstroms to about 13 Angstroms.

28. A composition in accordance with claim 1, wherein the average pore size is from about 3 Angstroms to about 10 Angstroms.

* * * * *